(12) United States Patent  (10) Patent No.: US 6,470,888 B1
Matter  (45) Date of Patent: Oct. 29, 2002

(54) SYSTEM FOR IN VIVO STERILIZATION OF A RESPIRATORY CIRCUIT

(75) Inventor: Jean-Paul Matter, Cincinnati, OH (US)

(73) Assignee: Freya, LLC, Cincinnati, OH (US)

( * ) Notice: Subject to any disclaimer, the term of this patent is extended or adjusted under 35 U.S.C. 154(b) by 0 days.

(21) Appl. No.: 09/435,966

(22) Filed: Nov. 8, 1999

(51) Int. Cl.[7] .......................... A61M 16/00; A62B 9/06
(52) U.S. Cl. ........................ 128/207.14; 128/207.15; 128/207.16; 128/912
(58) Field of Search ................ 128/207.14, 207.15, 128/207.16, 204.18, 912; 422/22; 250/455.11, 492

(56) References Cited

U.S. PATENT DOCUMENTS

| | | | |
|---|---|---|---|
| 3,648,706 A | * 3/1972 | Holzer | .................. 128/395 |
| 4,834,087 A | 5/1989 | Coleman et al. | |
| 5,053,033 A | 10/1991 | Clarke | |
| 5,065,757 A | 11/1991 | Dragisic et al. | |
| 5,165,395 A | 11/1992 | Ricci | |
| 5,193,544 A | 3/1993 | Jaffe | |
| 5,240,675 A | 8/1993 | Wilk et al. | |
| 5,260,020 A | 11/1993 | Wilk et al. | |
| 5,503,143 A | 4/1996 | Marion et al. | |
| 5,507,284 A | 4/1996 | Daneshvar | |
| 5,565,685 A | 10/1996 | Czako et al. | |
| 5,598,840 A | * 2/1997 | Lund et al. | ............. 128/207.14 |
| 5,637,877 A | 6/1997 | Sinofsky | |
| 5,687,714 A | 11/1997 | Kolobow et al. | |
| 5,695,482 A | * 12/1997 | Kaldany | ..................... 604/280 |
| 5,855,203 A | 1/1999 | Matter | |
| 6,109,259 A | * 8/2000 | Fitzgerald | .............. 128/200.26 |

FOREIGN PATENT DOCUMENTS

| | | |
|---|---|---|
| DE | 1488018 | 9/1973 |
| EP | 0 466 334 A1 | 12/1991 |
| FR | 2244548 | 9/1974 |

OTHER PUBLICATIONS

*Polymer Degradation, Principles and Practical Applications,* W. Schnabel, Hanser International, pp. 112–131.
*Polymer Chemistry, An Introduction,* Second Edition, Malcolm P. Stevens, Oxford University Press 1990, pp. 130–131; pp.306–311.
*New Linear Polymers,* Henry Lee, Donald Stoffey, Kris Nevelle, McGraw–Hill Book Company, p. 93.
*Respiratory Care, A Guide to Clinical Practice,* George F. Burton, M.D., John E. Hodgkin, M.C. and Jeffrey J. Ward, M.Ed., R.R.T., Third Edition, J.B. Lippincott Company, 1991, pp. 501, 503.
Results of on–line search of Medline Express®, Records 1–71.
*Plastic Component Design,* Paul D. Campbell, 1996, Industrial Press Inc., pp. 117–119.
*Evidence for Dynamic Phenomena in Residual Tracheal Tube Biofilm,* British Journal of Anaesthesia, Jan. 1993, vol. 70, No. 1.

(List continued on next page.)

Primary Examiner—Aaron J. Lewis
Assistant Examiner—Darwin Erezo
(74) Attorney, Agent, or Firm—Dinsmore & Shohl LLP

(57) ABSTRACT

A system and method in vivo sterilization of a respiratory circuit. A breathing tube has a proximal end, a distal end and a lumen extending between the proximal and distal ends; a respirator and a synchronization mechanism. One or more light sources capable of emitting ultraviolet radiation irradiates at least a portion of the respiratory circuit, such as the breathing tube, thereby sterilizing the respiratory circuit. The synchronization mechanism controls the light sources to synchronize the sterilization relative to the patient's breathing cycle. Several mechanisms to irradiate the respiratory circuit and control ultraviolet radiation are included.

23 Claims, 9 Drawing Sheets

OTHER PUBLICATIONS

*Concise Clinical Study, Contaminated Condensate in Mechanical Ventilator Circuits,* Donald E. Craven, Theresa A. Goularte, Barry J. Make, Boston, Massachusetts, 1984, pp. 625–628.

*Effect of Aerosolization on Curability and Viability of Gram–Negative Bacteria,* J. F. Heidelberg, M. Shahmat, M. Levin, J. Rahman, G. Stelma, C. Grim and R. R. Colwell, Applied and Environmental Microbiology, Sep. 1997, vol. 63, No. 3, pp. 3585–3588.

*Nosocomical pulmonary infection: Possible etiologic significance of bacterial adhesion to endotracheal tubes,* Frank D. Somile, Thomas J. Marrie, Donald S. Prough, Cherri D. Hobgood, David J. Gower, Lawrence X. Webb, J. William Costeron, Anthony G. Gristina, Critical Care Medicine, 1986, vol. 14, No. 4, pp. 265–270.

*Ballard Medical Products® Trac Care®,* http://www.bmed.com/products trachcare.shtml, Dec. 2, 1998.

\* cited by examiner

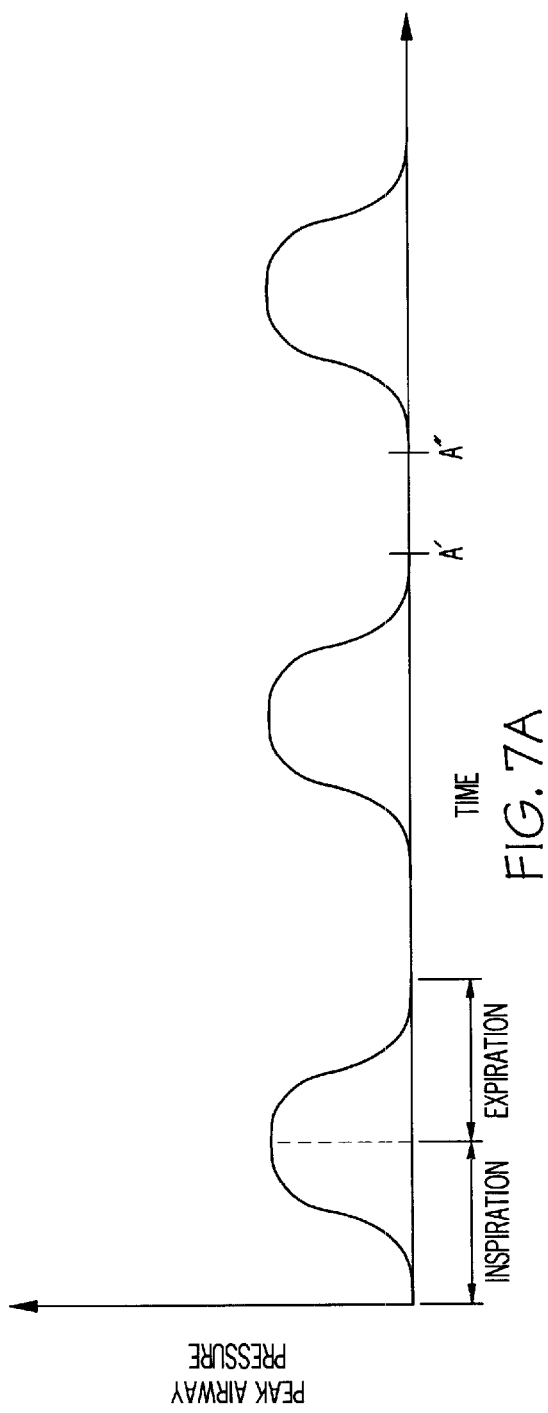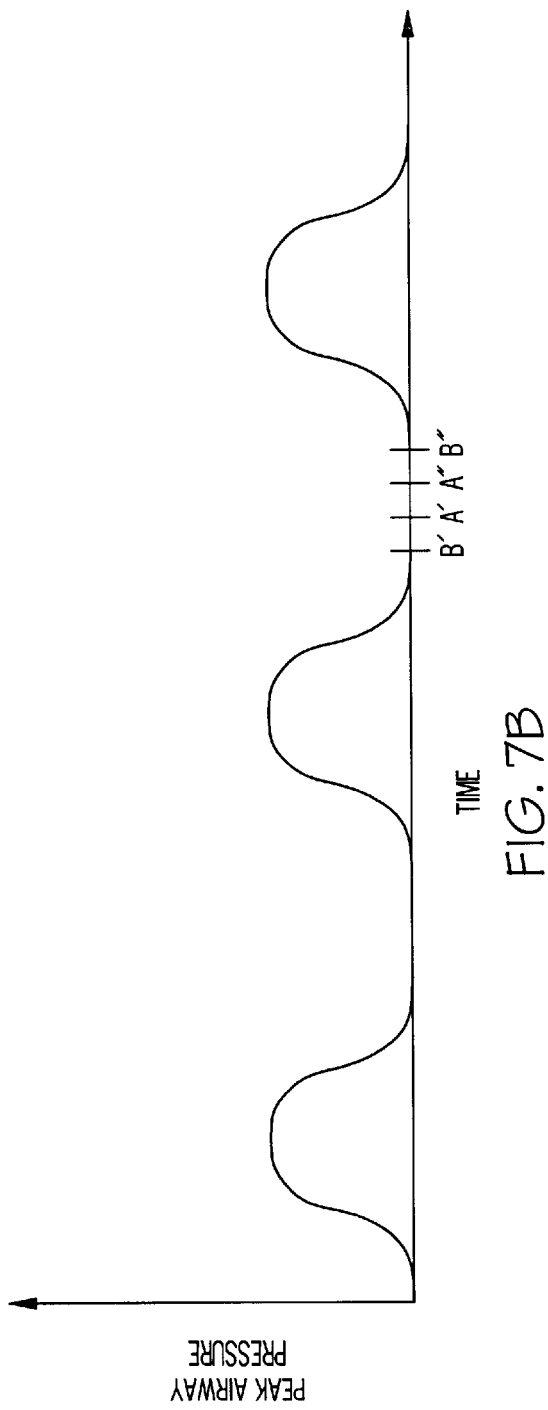

SYSTEM FOR IN VIVO STERILIZATION OF A RESPIRATORY CIRCUIT

TECHNICAL FIELD

The present invention relates generally to breathing devices, and will be specifically disclosed as a breathing tube and system capable of in vivo sterilization.

BACKGROUND

In many medical situations, the pulmonary functions (i.e., relating to the lungs) of a patient need to be monitored, controlled or accessed, and in many circumstances for days at a time. To achieve this, the medical field often uses a respiratory circuit which is connected to a ventilator, which is sometimes referred to as a respirator. Typically, respiratory circuits include a breathing tube (e.g., endotracheal tubes, tracheostomy tubes, laryngeal mask airways and the like) that acts as the interface between the patient and the respiratory circuit. For instance, an endotracheal tube is inserted through the mouth or nasal passage of the patient and into the trachea. Usually, a balloon or cuff surrounding the inserted end of the tube is inflated to provide a seal between the endotracheal tube and the trachea. Once sealed, the patient breathes through the endotracheal tube.

Once a breathing tube is connected to a patient, other components of the respiratory circuit are coupled to the breathing tube. Usually, a ventilator tube links the breathing tube with a ventilator which monitors, and if necessary can control, the pulmonary functions of the patient. Other components, such as junctions, moisture traps, filters, humidifiers and the like, optionally can be added to the respiratory circuit. For instance, drug delivery systems can be added to the respiratory circuit to deliver aerosolized medicine to the lungs of the patient. In some circumstances, medical caregivers require access to the lungs and/or trachea of the patient. For example, suction catheters are used to remove secretions in the patient's lungs. In such circumstances, special junctions can be added to the respiratory circuit which allows such access without interrupting the monitoring or control of the pulmonary functions.

An ongoing challenge with respiratory circuits is maintaining a sterile environment. Indeed, one clinical study has concluded that "trying to maintain a sterile ventilator circuit for 24 hours is a difficult and perhaps impossible task." Contaminated Condensate and Mechanical Ventilator Circuits, Donald E. Craven, et al., *Concise Clinical Study*, p. 627. Due to the inherent moisture and warmth, respiratory circuits provide superb conditions for microbiological growth and colonization. Once colonization has started, the microbiological growth can easily spread to the patient, either airborne or through moisture condensation running down into the patient's lungs, thus risking infections and complications, often resulting in pneumonia.

The problem of respiratory circuit colonization is especially prevalent within breathing tubes. For example, studies have documented the health risks from colonization in endotracheal tubes, sometimes referred to as a biofilm, which can be so extensive that the walls of the endotracheal tube become slimy and sticky. See Nosocomial Pulmonary Infection: Possible Etiologic Significance of Bacterial Adhesion to Endotracheal Tubes, Frank D. Sottile, et al., *Critical Care Medicine*, Vol. 14, No. 4, p. 265. Due to the close proximity to the patient's lungs, any microbiological growth in the breathing tube can easily spread to the patient's lungs. Condensed moisture can run down the breathing tube, over the biofilm and then to the patient's lungs. Additionally, chunks of the biofilm can actually fall off the breathing tube and into the patient's lungs.

SUMMARY OF THE INVENTION

Accordingly, an object of the invention is to provide a system for in vivo sterilization of a respiratory circuit. Additional objectives, advantages and novel features of the invention will be set forth in the description that follows and, in part, will become apparent to those skilled in the art upon examining or practicing the invention. The objects and advantages of the invention may be realized and obtained by means of the instrumentalities and combinations particularly pointed out in the appended claims.

One aspect of the present invention is a system for in vivo sterilization of a breathing tube. A breathing tube has a proximal end, a distal end and an inner surface defining a lumen extending between the proximal and distal ends. The breathing tube is operative to define at least a portion of a respiratory circuit for a patient having a breathing cycle. A respirator is in fluid communication with the breathing tube and is capable of monitoring the breathing cycle of the patient. One or more ultraviolet light sources are in optical communication with at least a portion of the inner surface of the breathing tube. The light sources emit ultraviolet radiation for sterilizing the irradiated portion of the inner surface while connected to a patient. A synchronization mechanism is in communication with the respirator and is capable of controlling the ultraviolet light sources. The synchronization mechanism is operative to intermittingly activate the ultraviolet light sources relative to the breathing cycle.

Another aspect of the present invention is an apparatus for in vivo sterilization of a breathing tube. The breathing tube has a proximal end, a distal end and a lumen extending between the proximal and distal ends through which a patient can breathe. A respiratory circuit junction has two or more openings at least one of which is dimensioned to connect with the proximal end of the breathing tube. A detachable housing defines a cavity and is configured to enclose a substantial portion of the respiratory circuit junction when the respiratory circuit junction is connected to the breathing tube. The detachable housing is substantially opaque to ultraviolet radiation. A source of ultraviolet radiation is in the cavity of the detachable housing and is positioned so as to irradiate the lumen of the breathing tube and sterilize the lumen.

Still another aspect of the present invention is a method of in vivo sterilization of a breathing tube. A breathing tube has a flow passage through which a patient can breathe is connected to the patient. The breathing cycle of the patient is monitored. The breathing cycle has a plurality of inhalation portions, a plurality of exhalation portions, and a transitional period between exhalation and inhalation portions. One or more ultraviolet light sources are provided. A flow passage of the breathing tube is obstructed during a transitional period of the breathing cycle between an exhalation portion and an inhalation portion. At least one of the ultraviolet sources is activated while the flow passage is obstructed such that the ultraviolet radiation sterilizes the flow passage of the breathing tube and the obstruction in the flow passage prevents ultraviolet radiation from exiting the breathing tube. The ultraviolet radiation sources are then deactivated. The flow passage of the breathing tube is then unobstructed during the transitional period before the inhalation portion of the breathing cycles starts.

Yet another aspect of the present invention is a system for in vivo sterilization of at least a portion of a respiratory circuit. A breathing tube is connected to a patient. The breathing tube has inner surface defining a flow passage through which the patient can breathe. A ventilator tube is in fluid communication with the breathing tube and a ventilator. The ventilator tube has an inner surface defining a flow passage through which the patient can breathe. One or more ultraviolet radiation sources are positioned so as to irradiate at least a portion of the inner surface of the ventilator tube such that the irradiated portions of the inner surface are sterilized. A jacket surrounds a substantial portion of the ventilator tube and has an inner surface facing the ventilator tube. The jacket is opaque to ultraviolet radiation and is positioned relative to the ultraviolet radiation sources such that ultraviolet radiation emitted from the ultraviolet radiation sources is prevented from exiting the jacket.

Still other aspects of the present invention will become apparent to those skilled in the art from the following detailed description which is by way of illustration one of the best modes contemplated for carrying out the invention. As will be realized, the invention is capable of other different and obvious aspects, all without departing from the invention. Accordingly, the drawings and descriptions are illustrative in nature and not restrictive.

BRIEF DESCRIPTION OF THE DRAWINGS

The accompanying drawings, incorporated in and forming part of the specification, illustrate several aspects of the present invention and, taken with the descriptions, serve to explain the principles of the invention. The present invention as set forth in the detailed description will be more fully understood when viewed in connection with the drawings in which:

FIG. 7A and FIG. 7B depict breathing cycles of a patient having a plurality of inspiration and expiration portions;

Reference will now be made in detail to various embodiments of the invention, an example of which is illustrated in the accompanying drawings, wherein the numerals indicate the same element throughout the views.

DETAILED DESCRIPTION

Figure 1:
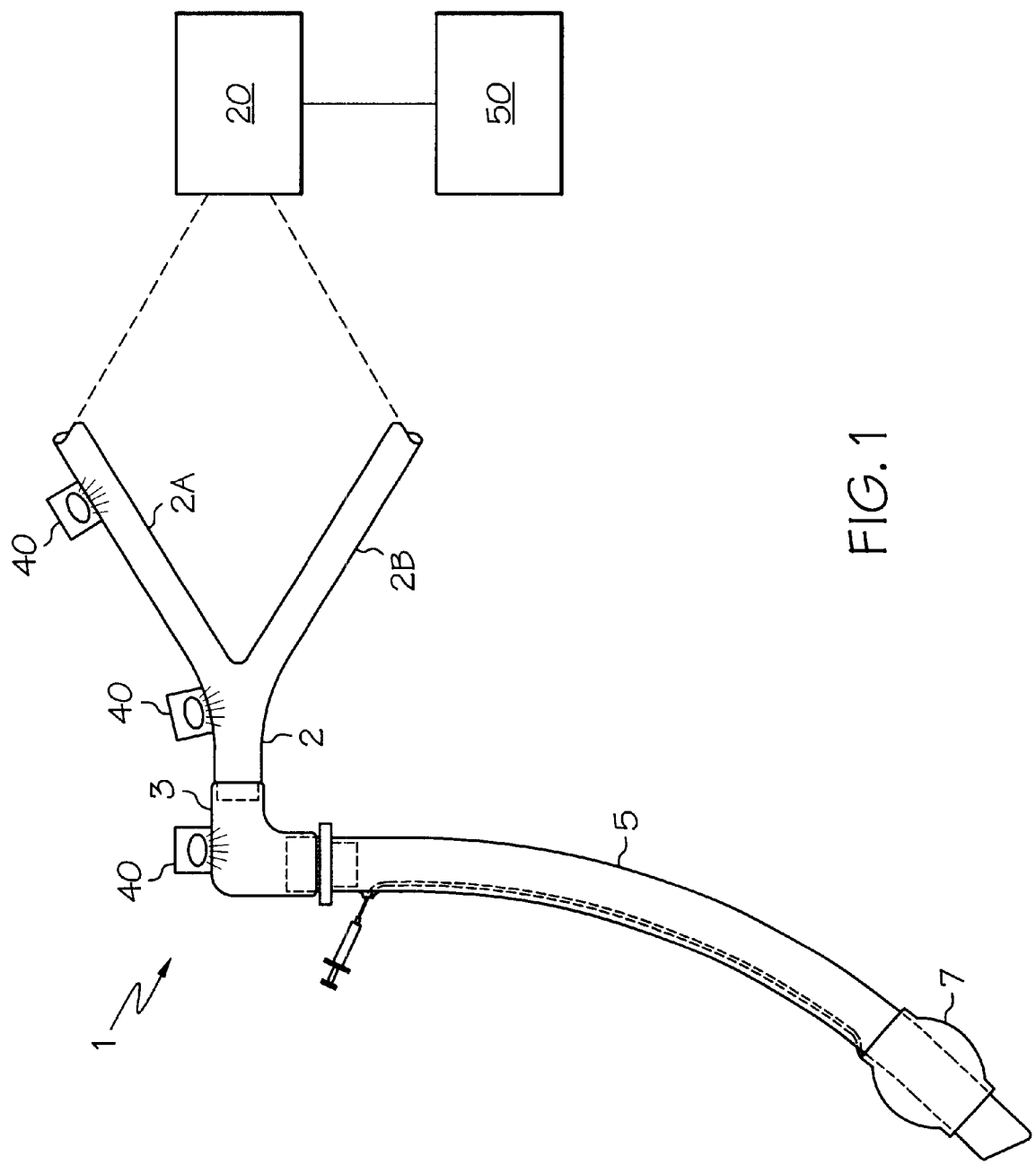
FIG. 1 depicts a schematic view of a system for in vivo sterilization of a respiratory circuit.

One embodiment of the present invention is depicted in FIG. 1, which illustrates an example of a respiratory circuit 1. A breathing tube, shown here as an endotracheal tube 5, forms a portion of the respiratory circuit 1. The endotracheal tube 5 is inserted through the mouth or nasal passages of the patient and into the trachea. Once inflated, the outer cuff 7 provides a seal between the endotracheal tube 5 and the trachea. Once sealed, the patient breathes through the endotracheal tube 5. A ventilator tube 2 also forms a portion of the respiratory circuit 1. The ventilator tube 2 includes an exhalation portion 2A and an inhalation portion 2B. The ventilator tube 2 is connected to a respirator 20 (sometimes referred to as a ventilator), which can be used to monitor and/or control the pulmonary functions of a patient. Valves and control mechanisms in the respirator 20 direct whether the exhalation portion 2A or the inhalation portion 2B will be used during a breath cycle. The ventilator tube 2 is in fluid communication with the breathing tube 5 through the junction 3. A variety of additional components can be included in the respiratory circuit 1, such as moisture traps, filters, humidifiers, suction catheters, and the like.

One or more light sources 40 are positioned so as to irradiate at least a portion of the respiratory circuit 1. The light sources 40 can remain on at all times while the respiratory circuit 1 is in use, or alternatively could be intermittently activated. The light sources 40 emit ultraviolet radiation which sterilizes those portions of the respiratory circuit 1 that are being irradiated as well as the air flowing in the respiratory circuit 1. Preferably, the light sources 40 will emit light ranging from 200 to 400 nanometers in wavelength. As disclosed in U.S. Pat. No. 5,855,203, which is incorporated by reference herein in its entirety, ultraviolet radiation is capable of sterilizing both airborne and surface microbiological growth in a respiratory circuit. For instance, studies have indicated that the sterilization efficacy of ultraviolet radiation in standard airflow conditions (0.5 second irradiation) were found to be over 99.5% in *staphylococcus aureus, staphylococcus epidermidis, serratia marcescens, bacillus subtilis* (vegetative cell) and *bacillus subtilis* (spore), and 67% in *aspergillus niger* (conidium). In *aspergillus niger*, which was the most resilient microbe to ultraviolet radiation, the efficacy rose up to 79% when irradiated for one second.

Figure 2:
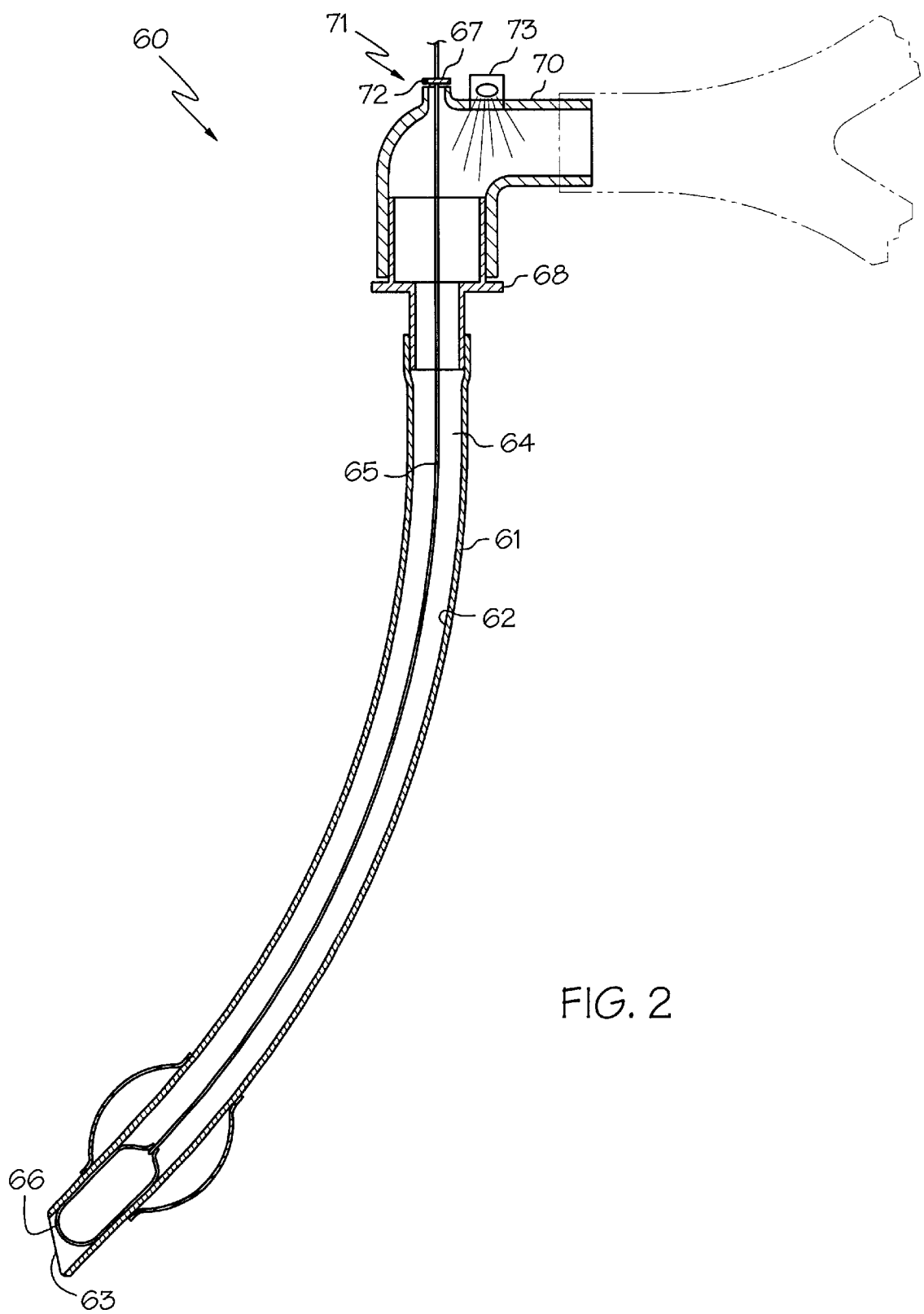
FIG. 2 depicts an endotracheal tube capable of in vivo sterilization using a balloon catheter.

A variety of different configurations can be employed to irradiate the endotracheal tube 5 with ultraviolet radiation to sterilize the endotracheal tube 5. Regardless of how ultraviolet light is introduced to the endotracheal tube, it is desirable to prevent the ultraviolet light from impinging upon the patient. FIG. 2 depicts one configuration to prevent ultraviolet light in the endotracheal tube 60 from escaping through the distal end 63. The endotracheal tube 60 comprises a tube wall 61 which is connected to the interface 68, and the interface 68 is connected to a junction 70 having a catheter port 71. When the endotracheal tube 60 requires sterilization, the balloon catheter 65 is inserted through the port 71 and into the lumen 64. The balloon catheter 65 includes an inflatable balloon 66, preferably made from an elastomeric material capable of blocking ultraviolet radiation. The balloon catheter 65 is connected to an inflation device (not shown), such as a syringe, pump, or the like, which can selectively inflate and deflate the balloon 66 with a pressurized fluid, such as air, water or the like. The balloon 66 should be in its deflated state when the balloon catheter 65 is being inserted and removed from the endotracheal tube 60 so that it may fit through the port 71 and lumen 64. Optionally, the balloon catheter 65 includes a bar 67, collar, or other blocking mechanism to assure that the balloon 66 is fully inserted into the endotracheal tube 60 and to prevent the balloon 66 from extending beyond the distal end 63. In one embodiment, the light source 73 will only illuminate when the bar 67 engages the contact 72 to complete an electrical circuit.

The junction 70 includes a light source 73 capable of emitting ultraviolet radiation, such as a xenon arc light, which is activated when the balloon catheter 65 is located in the endotracheal tube 60. The light source 73 is positioned such that the ultraviolet radiation will irradiate the lumen 64 of the endotracheal tube 60. Preferably, the tube wall 61 is substantially opaque to ultraviolet radiation to prevent leakage through the wall 61. The inner surface 62 of the tube wall 61 is preferably reflective such that the ultraviolet radiation will propagate towards the distal end 63 of the endotracheal tube, thus bathing the inner surface 62 with sterilizing ultraviolet radiation. When inflated, the balloon 66 prevents ultraviolet radiation from exiting through the distal end 63. Accordingly, the light source 73 should not emanate ultraviolet radiation unless the balloon 66 is inflated. Since the inflated balloon 66 can obstruct air flow through the lumen 64, the balloon 66 should be inflated during the time period between the expiration and inspiration of the patient, in which time period the balloon 66 is inflated, the light source 73 is activated to sterilize the inner surface 62 and then deactivated, and the balloon 66 is then deflated. The balloon catheter 65 with its deflated balloon 66 can then be removed from the endotracheal tube, and cleaned or discarded. The catheter port 71 can then be capped.

Figure 3:
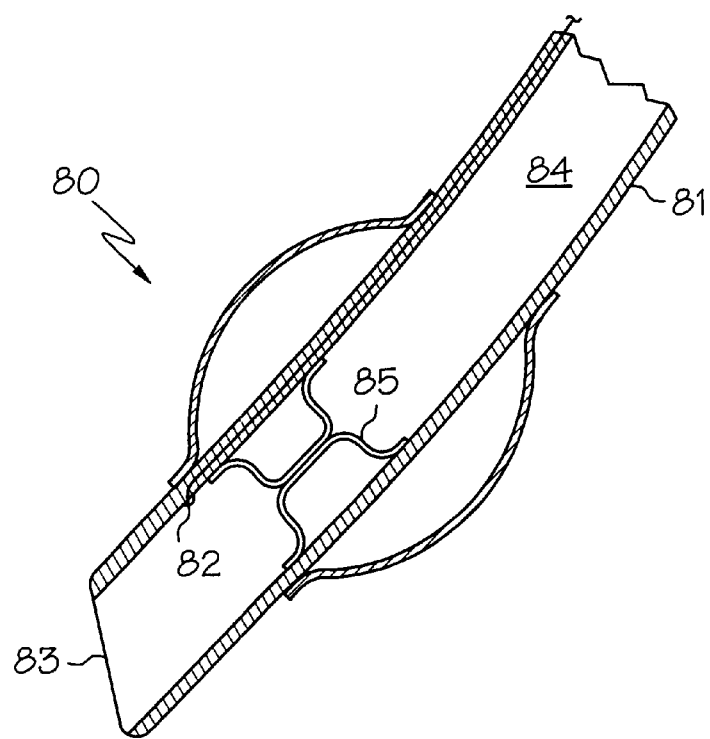
FIG. 3 depicts an endotracheal tube capable of in vivo sterilization using an inner cuff.

FIG. 3 depicts another configuration to prevent ultraviolet light in the endotracheal tube 80 from escaping through the distal end 83. When the endotracheal tube 80 requires sterilization, the inflatable cuff 85 is inflated (as shown) within the lumen 84. The inflatable cuff 85. is attached to the inner surface of the endotracheal tube 80, and is preferably made from an elastomeric material capable of blocking ultraviolet radiation. Accordingly, when inflated, ultraviolet radiation in the lumen 84 is blocked and prevented from escaping through the distal end 83 of the endotracheal tube 80. The inflatable cuff 85 is connected (such a tube in the wall 81) to an inflation device (not shown), such as a syringe, pump, or the like, which can selectively inflate and deflate the cuff 85 with a pressurized fluid, such as air, water or the like. Preferably, in the deflated state the deflation device will impart a negative pressure or vacuum on the cuff 85 such that the cuff will hug the tube wall 81 and minimize the obstruction of air flow through the lumen 84.

Preferably, endotracheal tube 80 further includes an ultraviolet radiation detector 82. The radiation detector 82 is located at or near the distal end 83 of the endotracheal tube 80, preferably on the distal side of the cuff 85. The ultraviolet radiation detector 82 is in communication with a control device (not shown) such as the synchronization mechanism 50 for the ultraviolet light source (also not shown). When a threshold amount of ultraviolet radiation is detected by the detector 82, the control device preferably terminates the light so as to prevent any ultraviolet radiation from exiting the distal end 83.

Figure 4:
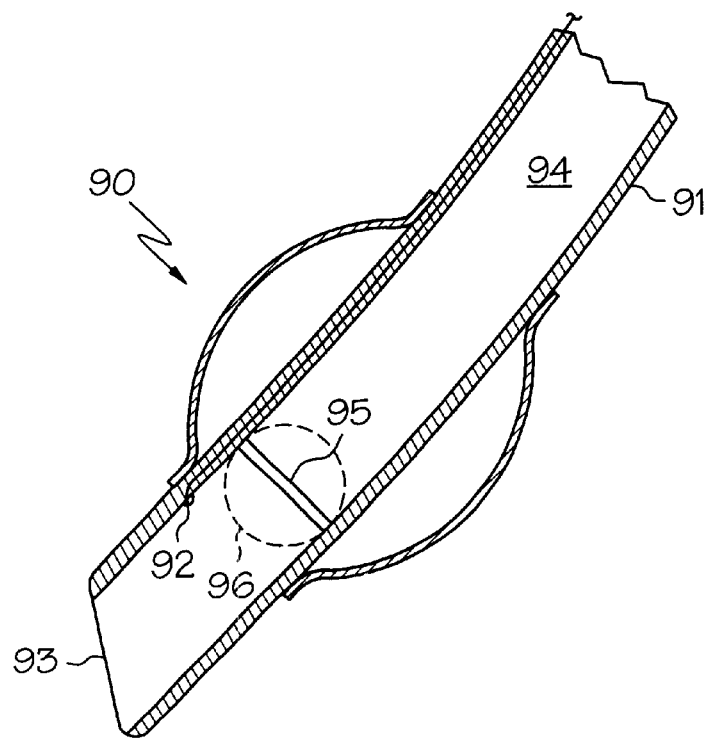
FIG. 4 depicts an endotracheal tube capable of in vivo sterilization using a shutter.

FIG. 4 depicts another configuration to prevent ultraviolet light in the endotracheal tube 90 from escaping through the distal end 93. The endotracheal tube 90 has a tube wall 91 similar to the tube wall 81. Located near the distal end 93 is a shutter 95, which operates much like a butterfly valve. The shutter 95 may be operated using a variety of mechanisms, including pneumatics, electromagnetic fields, cabling, and other means known in the art. In the opened position 96 (shown in phantom), the lumen 94 is substantially unobstructed such that air may readily pass in the lumen 94. Preferably, the shutter 95 will be biased (e.g. via a spring, elastomer or the like) in the opened position 96. When the endotracheal tube 90 requires sterilization, the shutter 95 is moved to its closed position (as shown) within the lumen 94. The shutter 95 is preferably made from a material capable of blocking ultraviolet radiation. Accordingly, when the shutter 95 is closed, ultraviolet radiation introduced to the lumen 94 is blocked and prevented from escaping through the distal end 93 of the endotracheal tube 90. Optionally, the shutter 95 is constructed of a material having sufficient air permeability that breathing may continue even if the shutter 95 is in the closed position. As shown here, an ultraviolet detector 92 is provided, which is similar to the detector 82. Preferably, the axis of rotation for the shutter 95 is off center from the tube 90, such that if a patient attempts to breathe while the shutter 95 is closed, the pressure induce by the breath on the shutter 95 will move the shutter 95 to its opened position. In one embodiment, the shutter 95 will rupture if a predetermined threshold stress is experienced. Preferably, sensors are positioned to detect whether the shutter 95 is opened by a patient's breath or the shutter 95 ruptures, and appropriate alarms will be signaled.

Figure 5:
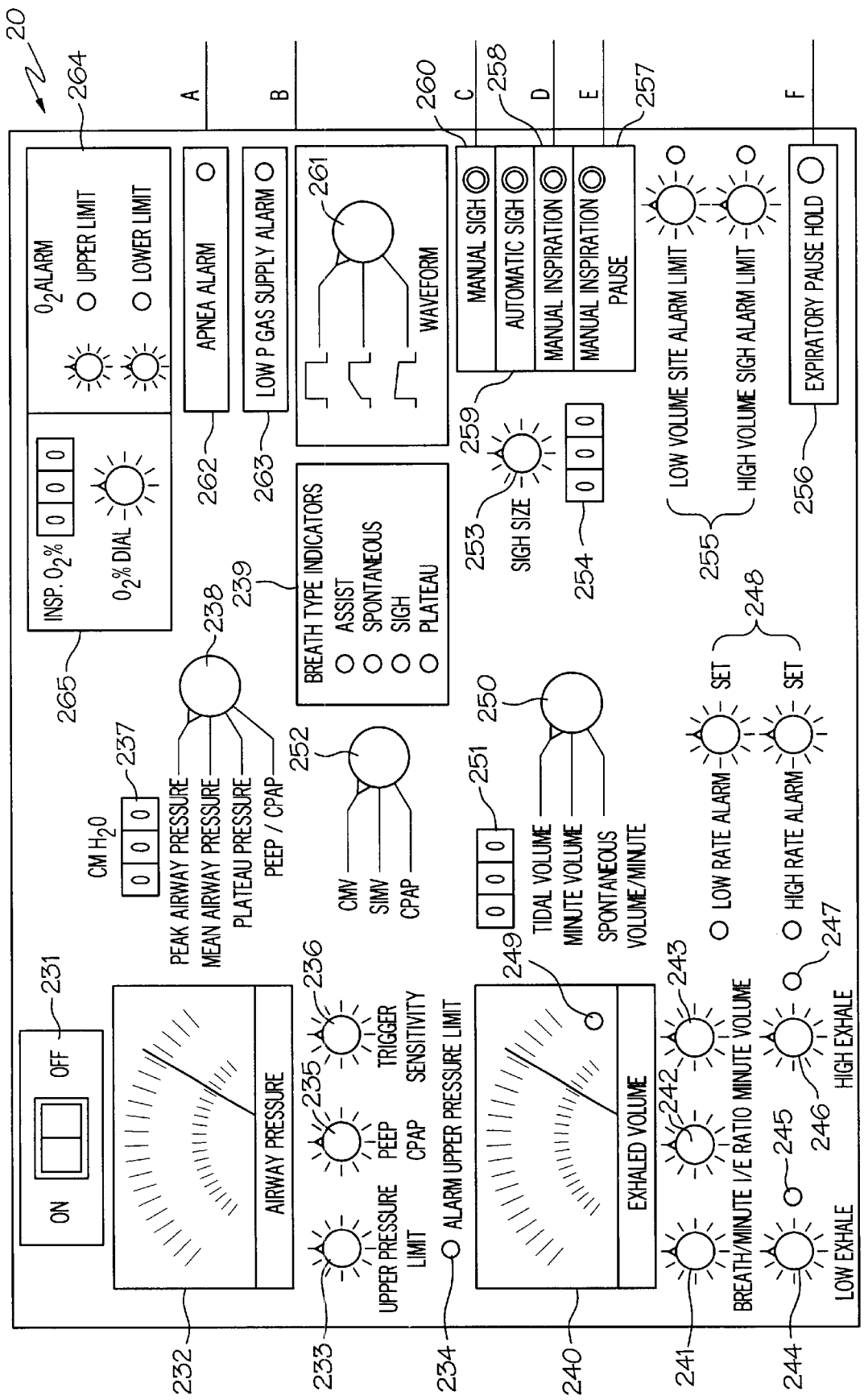
FIG. 5 depicts a generic respirator.

FIG. 5 shows a generic ventilator 20. The generic ventilator schematizes any current ventilator, such as the Bear 2,3 (Bear Medical Systems®, the Bennett 7200A Series (Puritan Bennett CRP®, the Ohmeda Advent ventilator and the Ohmeda TM Modulus series (Ohmeda Corp®), the Siemens Elema Servo Ventilator 900 series (Siemens Elema®), and the like. One with ordinary skill in the art will readily appreciate how to use the generic respirator 20. By way of summary, however, the following brief description explains the ventilator:

231: ON OFF switch, with transparent plastic lid cover
232: analogue airway pressure display
233: upper pressure limit alarm dial
234: upper pressure limit alarm light
235: PEEP (positive end expiratory pressure), CPAP (constant positive airway pressure) control dial set.
236 : inspiratory trigger sensitivity.
237: digital display in cm of water
238: dial for the display of different airway pressure
239: breath type indicator display
240: exhaled volume in liter /minute, analogue display
241: breath per minute dial set.
242: inspiratory /expiratory ratio dial set.
243: minute volume dial set.
244: low exhaled minute volume alarm dial set.
245: LED alarm low exhaled volume.
246: high exhaled minute volume alarm dial set.
247: LED alarm high minute volume.
248: rate alarm assembly set.
249: volume alarm LED
250: dial for LED display of volume parameters
251: LED display for volume parameter dial 250.
252: respiratory mode dial CMV (controlled mechanical ventilation) IMV (intermittent mandatory ventilation) CPAP (continuous positive airway pressure).
253: Sigh volumetric control dial.
254: LED display of sigh size.
255: volumetric sigh alarm control display.
256: expiratory pause hold button, also remotely controlled with connection F.
257: manual inspiratory pause hold button, also remotely controlled with connection E.
258: manual inspiration button, also remotely controlled with connection D.
259: automatic sigh button (ON OFF) one breath in 100 is a sigh.
260: manual sigh button, also remotely controlled with connection C.
261: inspiratory waveform control dial
262: apnea alarm LED
263: low pressure gas supply alarm LED 264: oxygen alarm module.
265: inspiratory oxygen control module.
Connection A: respiratory mode DATA.
Connection B: digital data from airway pressure transducer.

The embodiments illustrated in FIGS. 2, 3 and 4 all include means for preventing ultraviolet radiation from exiting through the distal end of the breathing tube (e.g. the inflatable balloon 66, inflatable cuff 85 and shutter 95). The blocking means can reduce airflow through the breathing tube, so it is preferred that the means for blocking only be activated during the transitional period between an exhalation and inhalation of the patient. Since the timing of the activation/deactivation of the blocking mechanism and ultraviolet radiation sources with respect to the breathing cycle of the patient can be somewhat complex, it is preferred that such steps be undertaken by an automated system, such as the synchronization mechanism 50.

Figure 6:
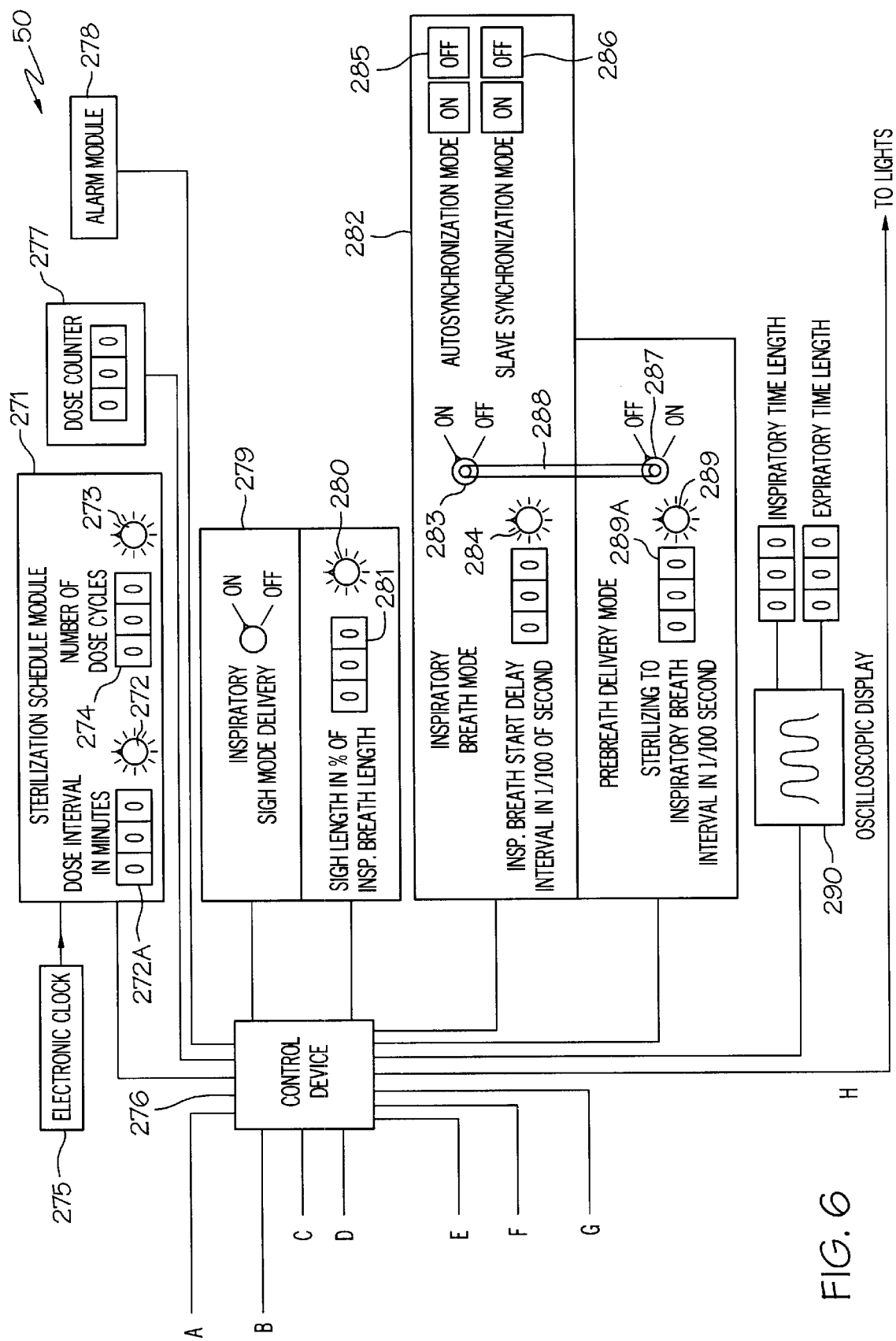
FIG. 6 depicts a synchronization mechanism.

FIG. 6 shows an example of a synchronization mechanism 50 which communicates with the respirator 20 either as an integral part of the respirator 20 or as a separate component. The synchronization mechanism 50 is connected to and configured to control the lights 40, preferably intermittently, relative to the breathing cycle of the patient as monitored by the respirator 20. The synchronization mechanism 50 provides several options for a clinician to program the in vivo sterilization of a breathing tube. The clinician prescribes a sterilizing schedule on the sterilization module 271. First, the clinician prescribes the interval dose in minutes (ex: 4H=240 minutes), with the number being selected on the dial 272. An LCD display shows the number of minutes 272A. For instance, it is believed that a dose of ultraviolet radiation once every hour will prevent colonization in the breathing tube, and as such reduce the risk of pulmonary infections. Naturally, however, the frequency of doses may be varied, as may be needed.

The clinician can prescribe the number of sterilizing cycles. He dials the number on the dial 273, the LCD display 274 shows the number. An electronic clock 275 paces the sterilization module. The sterilization schedule is transmitted to the control device 276, which routes information to and from the respirator 20. A dose counter 277 keeps an accurate number of the total doses. An alarm module 278 will alarm if there is a discrepancy between the prescribed doses and the ones actually delivered.

Optionally, the clinician can select the different types of delivery modes. First he can select sterilizing with inspiratory sigh mode on module 279: ON/OFF. He can prolong the sigh time on the dial 280 to a maximum, such as 150% of inspiratory breath length. An LCD displays the length of the prescribed sigh 281.

In the present embodiment, the clinician can select the time of the sterilizing in the respiratory cycle. On module 282 he can choose sterilizing with inspiratory breath mode 283 ON/OFF. He dials the interval between the inspiratory breath and start of the sterilizing in 1/100 second intervals on dial 284. He can also select the auto synchronization mode ON/OFF 285 where the respirator paces the inspiratory breath. Alternatively, he can use the slave synchronization mode ON/OFF 286 where the control device 276 fires the next breath. Only one of the two modes 285 and 286 can be on at any time.

The clinician can use the prebreath delivery mode on the module 287 OFF/ON. Since only one mode can be chosen between the mode 283, 287, a correlation mechanism 288, such as a linking chain, will keep the module 287 ON only if the mode 282 is OFF, and vice versa. The sterilizing during the inspiratory breath interval can be dialed on the dial 289. A LCD display shows the interval in 1/100 sec 289A.

An oscilloscope 290 displays the airway pressure in relation to time. A LCD display module displays the inspiratory time length and the expiratory time length. The control device gets the respiratory mode data with line a, the transduced airway pressure data with line B. This connection is used to time the sterilizing with the respiratory cycle and to detect the expiratory pause. The in vivo sterilization system could use any other type of signal which detects a expiratory pause, such as: an end tidal CO2 analyzer, an apnea monitor of any type, or the like. The link to the manual sigh control switch is contained in connection C, the manual inspiration switch link is contained in connection D, the inspiratory pause switch link is contained in connection E, the manual expiratory pause switch link is contained in connection F. Connection G is a link from the control device to a remote DATA site. Connection H is the link of the control device to the lights 40.

In a preferred embodiment, the synchronization mechanism 50 comprises a programmable computer unit. The computer can be programmed to activate the ultraviolet light sources 40 when desired. A computer is a general-purpose machine that processes data according to a set of instructions that are stored internally either temporarily or permanently. The computer and all equipment attached to it are called hardware. The instructions that tell the computer what to do are called software. A set of instructions that perform a particular task is called a program or software program. The instructions in the program direct the computer to input, process and output. The computer can selectively retrieve data into its main memory (RAM) from any peripheral device (terminal, disk, tape, etc.) connected to it. The data is then processed by the Central Processing Unit (CPU). Once the data is in the computer's memory, the CPU can process it by calculating, comparing and copying it. The computer can perform any mathematical operation on data by adding, subtracting, multiplying and dividing one set with another. The computer can analyze and evaluate data. After processing the data internally, the computer can send a copy of the results from its memory to any peripheral device. By outputting data onto a magnetic disk, optical disk, flash memory, or other storage means, the computer is able to store data permanently and retrieve the data when required.

FIG. 7A illustrates an example of a breathing cycle of a patient. The breathing cycle can be monitored by visually observing the patient or automatically using a ventilator 20 The ultraviolet lights 40 can be activated at any time during the breathing cycle to sterilize any portion of the respiratory circuit. If the lights are intermittently activated, with respect to the breathing tube, it is preferred that the sterilizing light be activated during the transitional period between an exhalation and an inhalation. In the present example, the ultraviolet light that sterilizes the breathing tube is activated at point A' and deactivated at point A".The activation and deactivation of the lights 40 are preferably controlled by the synchronization mechanism 50, but can also be controlled manually. FIG 7B illustrates another example of a breathing cycle, If a blocking mechanism is used in the breathing tube (e.g. balloon 66, cuff 85, shutter 95, or the like), it is preferred that the blocking mechanism be closed only during the transitional period between an expiration and an inspiration. As illustrated in the present example, the blocking mechanism is closed at point B', immediately after an expiration. The ultraviolet light source is then activated and deactivated at points A' and A", respectively, and the blocking mechanism is then opened at point B". Accordingly, the flowpath of the breathing tube is blocked only during the transitional period when the breath cycle is motionless, thus preventing interference with the patient's breathing cycle.

Figure 8:
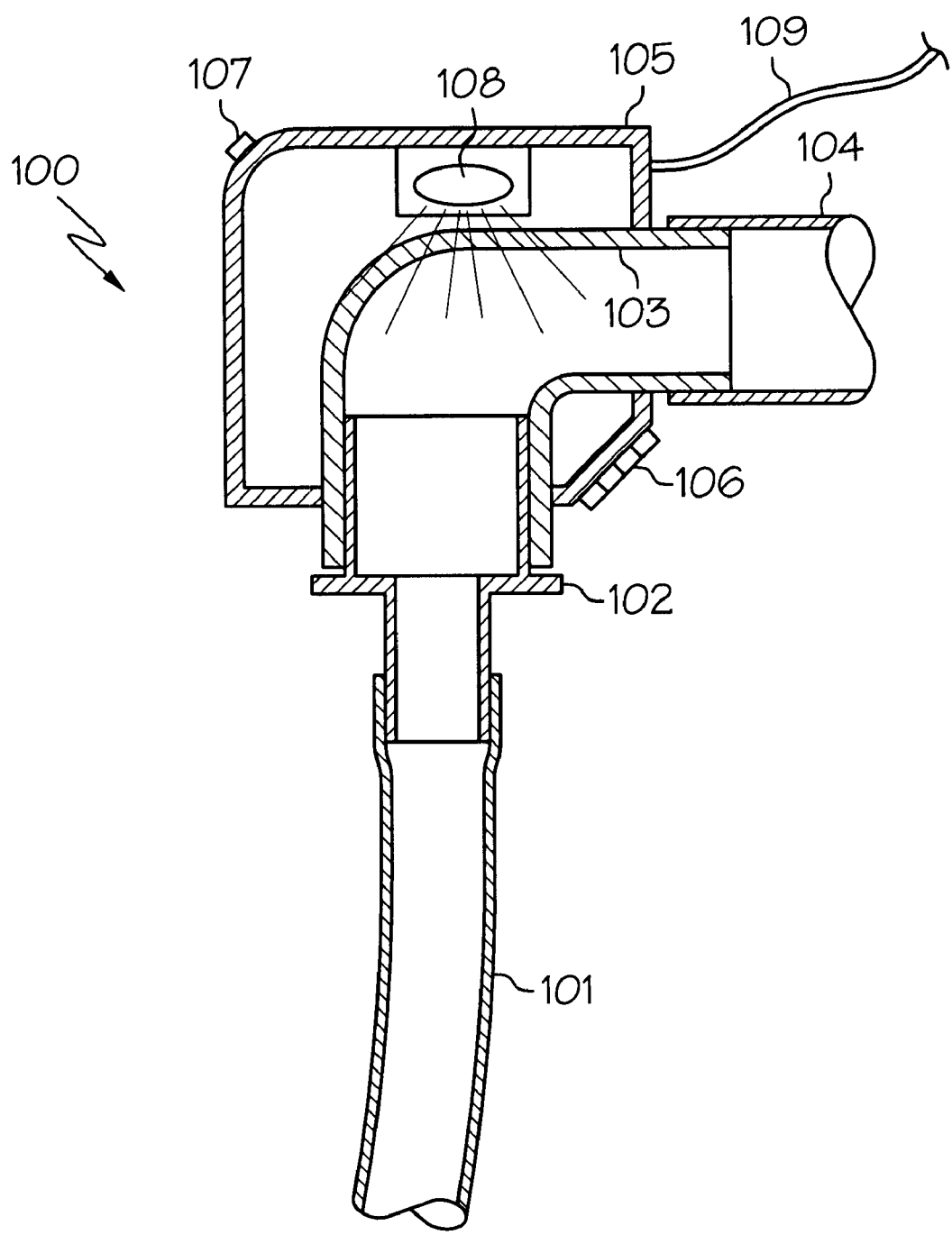
FIG. 8 depicts a detachable housing for a respiratory circuit junction.

FIG. 8 depicts an apparatus 100 for in vivo sterilization of a breathing tube 101. A detachable housing 105 is configured to enclose the respiratory circuit junction 103. An interface 102 is connected to respiratory circuit junction 103, which in turn is connected to the ventilator line 104 and the breathing tube 101. A communication link 109, such as a wire, optical fiber, radio wave, optical signal, or the like, connects the detachable housing 105 to a controller (not shown), such as a respirator 20 or a synchronization mechanism 50. The detachable housing 105 further comprises one or more ultraviolet light sources 108 and one or more pieces forming a cavity. In the present example, the housing has two halves connected by the hinge 106. The housing 105 may readily be attached and detached from the junction 103. The clasp 107 holds the two halves together. Preferably, the ultraviolet light source 108 is connected directly to the housing 105 and takes the form of a xenon flash lamp. Ideally, the housing 105 is made of an ultraviolet opaque material to prevent ultraviolet radiation from leaving the housing 105. The light source 108 is positioned such that it may irradiate through the junction 103 and into the breathing tube 101 to sterilize the breathing tube 101. Accordingly, the housing 105 may be attached and used only when sterilization of the breathing tube 101 is desired. Between sterilization doses, the housing 105 may be removed.

Figure 9:
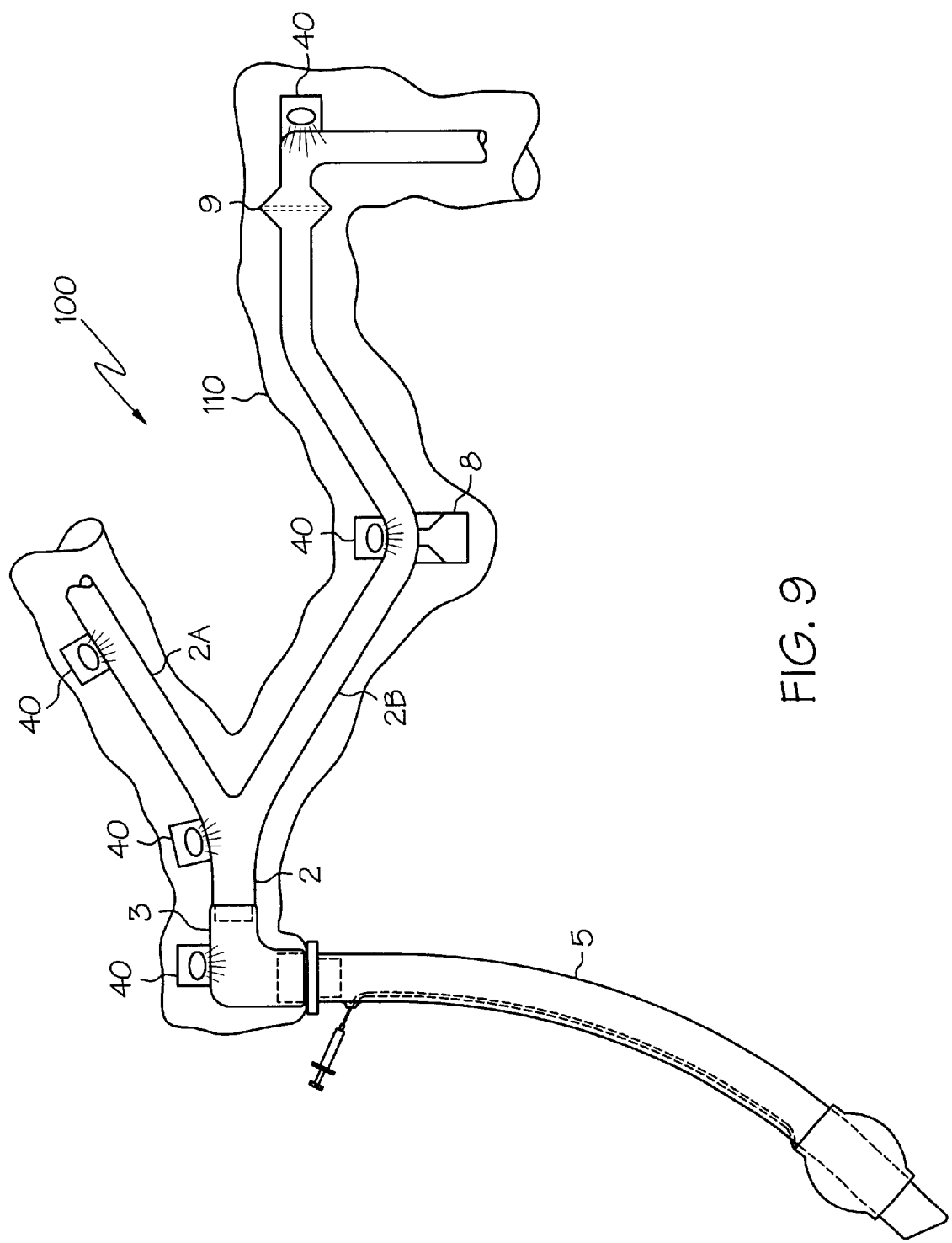
FIG. 9 depicts a respiratory circuit with an ultraviolet opaque jacket.

FIG. 9 illustrates a system 100 for in vivo sterilization of a respiratory circuit. The respiratory circuit includes an endotracheal tube 5, a junction 3, ventilator tube 2, as well as other components, such as the moisture trap 8 and a filter 9. A variety of light sources 40 are capable of emitting ultraviolet radiation to irradiate various portions of the respiratory circuit. A jacket 110 surrounds various portions of the respiratory circuit. As shown in this example, the jacket 110 surrounds the junction 3, ventilator tube 2 (including the exhalation portion 2A and inhalation portion 2B). Additional components of a respiratory circuit may also be surrounded by the jacket 110, including moisture traps, filters, humidifiers, suction catheters, nebulizers, junctions, and the like. Preferably, the jacket 110 is opaque to ultraviolet radiation. Accordingly, the ultraviolet radiation emitted by the light sources 40 will be contained within the jacket 110, thus preventing the irradiation of the patient, medical personnel, or other equipment. While the jacket 110 is preferably opaque to ultraviolet radiation, it is further preferred that the jacket 110 nevertheless be transparent to at least a portion of the visible light range. As such, medical personnel can view the respiratory circuit while still be shielded from the ultraviolet radiation emitted by the light sources 40. In one embodiment, the inner surface of the jacket 110, which faces the respiratory circuit, is reflective to ultraviolet radiation so as to facilitate the propagation and increased bathing of ultraviolet radiation across the respiratory circuit for sterilization purposes. As shown in this example, the jacket 110 is made of a flexible material, however, more rigid materials are also contemplated. The jacket 110 can be an integral part of the respiratory circuit or it can be removable and/or reusable. While in this example the entire ventilator tube 2 is surrounded by the jacket 110, it is also contemplated that only a portion of the ventilator tube be surrounded.

Figure 10:
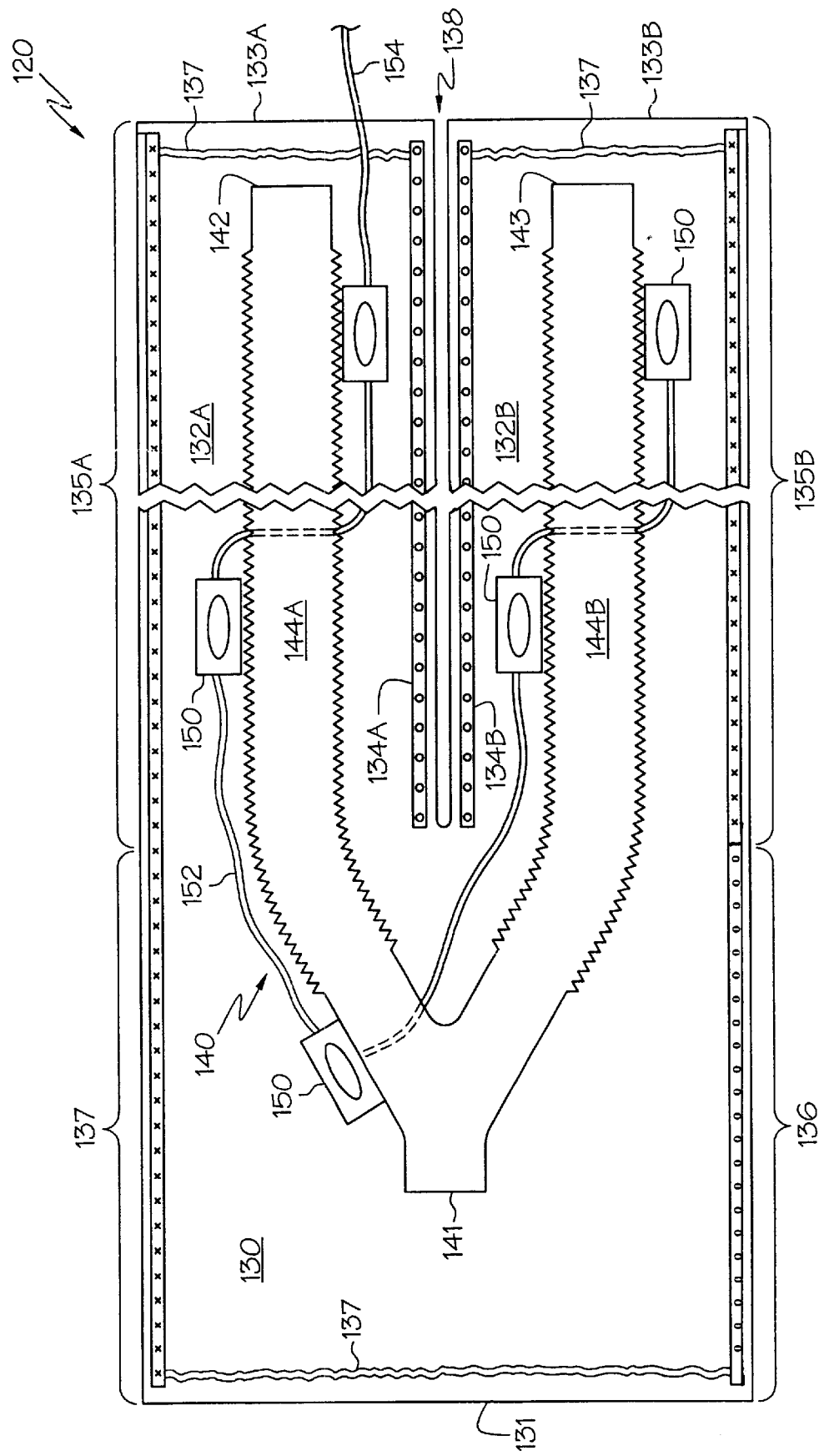
FIG. 10 depicts a flexible shroud for jacketing a ventilator tube.

FIG. 10 illustrates an example of a system 120 for in vivo sterilization of a respiratory circuit. In this example, the flexible shroud 130 acts as a jacket to surround the ventilator tube 140. As shown in this figure, the shroud 130 is in an opened state to illustrate the assembly of the shroud 130 relative to the ventilator tube 140. The ventilator tube 140 is a "Y" shaped tube having an exhalation leg 144A and an inhalation leg 144B. The common port 141 is dimensioned to be connected to a respiratory circuit junction, breathing tube or other respiratory circuit apparatuses. The exhalation leg 144A terminates with the port 142, and the inhalation leg 144B terminates with the port 143. In the present example, the shroud 130 is a generally elongated rectangular sheet of material, which is preferably opaque to ultraviolet radiation but transparent to a portion of the wavelengths of visible light. The shroud 130 is cut along a portion of its length resulting in a slit 138 defining two legs 132A, 132B.

In use, the shroud 130 is laid flat on a surface with a ventilator tube 140 placed on the shroud 130, substantially as shown. Other components of a respiratory circuit may additionally be connected to the ventilator tube 140. One or more ultraviolet light sources 150 are attached to the ventilator tube 140. The lights 150 are connected to one another with a wire 152 having an end 154 connected to a control device (not shown) capable of controlling the activation of the light sources 150. In the present embodiment, the shroud 130 utilizes several fastening mechanisms to surround the ventilator tube 140 and light sources 150. For instance, VELCRO strips are attached to the shroud 130 at strategic locations. The looped sections 134A, 134B are designed to be attached to the hooked sections 135A, 135B, respectively. The looped section 136 is intended to be connected to the hooked section 137. While the hooked and looped connection mechanism found in VELCRO are preferred, a variety of other fastening mechanisms are also contemplated included, zippers, buttons, tapes, adhesives, and the like. Preferably, selective portions of the fastening mechanism can be detached to access the ventilator tube 140, the light sources 150, or other components of the respiratory circuit contained within the shroud 130. The shroud 130 also includes various mechanisms to bias the flexible shroud 130 against the respiratory tube 140 such that the shroud 130 will closely hug the respiratory tube 140. In the present example, three elastic strips 137 are attached to the shroud 130 at strategic locations. The elastic strips 137 provided near the ends so as to prevent ultraviolet radiation within the shroud from escaping. While not shown in this figure, biasing mechanisms can be placed at other locations along the length of the shroud 130 so as to prevent excessive bagginess around the ventilator tube 140. It should be noted that alternative biasing mechanisms are also contemplated including drawstrings, tapes, VELCRO and the like.

Throughout the foregoing specification, the materials used in the junctions, ventilator tubes, breathing tube, etc. are designed to be irradiated with ultraviolet radiation, which can be destructive to many materials. As such, preferable materials will be resistant to ultraviolet radiation, either through their inherent qualities, such as TEFLON®, or through additives such as ultraviolet absorbers or antioxidants. While one with ordinary skill in the art will be capable of selecting such preferred materials or additives, the following references may be helpful: *Polymer Degradation Principles and Practical Applications* by W. Schnabel, *Polymer Chemistry an Introduction*, 2nd ed., by Malcolm P. Stevens, *New Linear Polymers* by Henry Lee, et al., and *Plastic Component Design* by Paul Campbell, which references are hereby incorporated by reference.

The foregoing descriptions of the various embodiments of the invention has been presented for the purposes of illustration and description. It is not intended to be exhaustive or to limit the invention to the precise form disclosed. Many alterations, modifications, and variations will be apparent to those skilled in the art of the above teaching. Accordingly, this invention is intended to embrace all alternatives, modifications, and variations that have been discussed herein, and others that fall within the spirit and broad scope of the claims.

What is claimed is:

1. A breathing tube system comprising:
   a) a breathing tube having a proximal end, a distal end, and an inner surface defining a lumen extending between the proximal and distal ends, said breathing tube being operative to define at least a portion of a respiratory circuit for a patient having a breathing cycle;
   b) a respirator in fluid communication with the breathing tube and being capable of monitoring the breathing cycle of the patient;
   c) one or more ultraviolet light sources in optical communication with at least a portion of the inner surface of the breathing tube, said one or more light sources emitting ultraviolet radiation for sterilizing an irradiated portion of the inner surface while connected to a patient; and
   d) a synchronization mechanism in communication with the respirator and capable of controlling the one or more ultraviolet light sources, said synchronization mechanism being operative to intermittently activate the ultraviolet light sources relative to the breathing cycle.

2. The system of claim 1, further comprising means for preventing ultraviolet radiation from exiting the distal end of the breathing tube.

3. The system of claim 2, wherein the preventing means is in communication with the synchronization mechanism, and the synchronization mechanism being further operative to control the preventing means relative to the breathing cycle.

4. The system of claim 2, wherein the preventing means comprises one or more inflatable portions positioned in the lumen of the breathing tube and dimensioned such that when inflated ultraviolet radiation is prevented from exiting the distal end of the breathing tube.

5. The system of claim 2, wherein the preventing means comprises a shutter having an opened position and a closed position, said shutter being positioned in the lumen of the breathing tube and dimensioned to inhibit ultraviolet radiation from exiting the distal end of the breathing tube when the shutter is in the closed position.

6. The system of claim 1, wherein the synchronization mechanism comprises a programmable computer unit connected to the respirator unit, the programmable computer unit being programmed to activate the ultraviolet light sources.

7. The system of claim 1, further comprising a means for detecting ultraviolet radiation exiting from the distal end of the breathing tube.

8. The system of claim 7, wherein the synchronization mechanism is further operative to terminate the ultraviolet light sources when ultraviolet radiation is detected exiting the distal end of the breathing tube.

9. A breathing tube apparatus comprising:
   a) a breathing tube having a proximal end, a distal end, and a lumen extending between the proximal and distal ends through which a patient can breath;
   b) a respiratory circuit junction having two or more openings, at least one of said openings being dimensioned to connect with the proximal end of the breathing tube;
   c) a detachable housing defining a cavity and being configured to enclose a substantial portion of the respiratory circuit junction when the respiratory circuit junction is connected to the breathing tube, said detachable housing being substantially opaque to ultraviolet radiation; and
   d) a source of ultraviolet radiation in the cavity of the detachable housing and being positioned so as to irradiate the lumen of the breathing tube and sterilize the lumen.

10. The apparatus of claim 9, wherein the detachable housing comprises two hinged halves.

11. The method of in vivo sterilization of a breathing tube, comprising the steps of:
    a) connection a breathing tube to a patient, the breathing tube having a flow passage through which the patient can breath;
    b) monitoring the breathing cycle of a patient, said breathing cycle having a plurality of inhalation portions, a plurality of exhalation portions, and a transitional period between each exhalation and inhalation portion;
    c) providing one or more ultraviolet radiation sources;
    d) obstructing the flow passage of the breathing tube during a transitional period of the breathing cycle between an exhalation portion and an inhalation portion;
    e) activating at least one of the ultraviolet radiation sources while the flow passage is obstructed, such that the ultraviolet radiation sterilizes the flow passage of the breathing tube and the obstruction in the flow passage prevents ultraviolet radiation from exiting the breathing tube;
    f) deactivating the ultraviolet radiation sources; and
    g) unobstructing the flow passage of the breathing tube during the transitional period before the inhalation portion of the breathing cycle starts.

12. The method of claim 11, wherein the monitoring comprises visual monitoring.

13. The method of claim 11, wherein the step of monitoring is performed by a respirator.

14. The method of claim 11, further comprising the step of programming a schedule for the in vivo sterilization of a breathing tube.

15. A system for in vivo sterilization of at least a portion of a respiratory circuit, the system comprising:
    a) a breathing tube adapted to be connected to a patient, said breathing tube comprising an inner surface defining a flow passage through which the patient can breath;
    b) a ventilator tube in fluid communication with the breathing tube and a ventilator, said ventilator tube comprising an inner surface defining a flow passage through which the patient can breath;
    c) one or more ultraviolet radiation sources positioned so as to irradiate at least a portion of the inner surface of the ventilator tube such that the irradiated portions of the inner surface of the ventilator tube are sterilized;
    d) a jacket surrounding a substantial portion of the ventilator tube and having an inner surface facing the ventilator tube, said jacket being opaque to ultraviolet radiation and being positioned relative to the ultraviolet radiation sources such that the ultraviolet radiation emitted from the ultraviolet radiation sources is prevented from exiting the jacket.

16. The system of claim 15, further comprising a junction positioned between the breathing tube and the ventilator tube, said junction being surrounded by the jacket.

17. The system of claim 15, wherein the inner surface of the jacket is reflective to ultraviolet radiation.

18. The system of claim 15, wherein the jacket is transparent to at least a portion of the visible range of light.

19. The system of claim 15, wherein the jacket is a flexible shroud.

20. The system of claim 19, wherein the flexible shroud is removable from the ventilator tube.

21. The system of claim 19, further comprising means for biasing the flexible shroud to engage the ventilator tube.

22. The system of claim 15, wherein the ventilator tube has an inspiration portion and an expiration portion, the jacket being dimensioned to surround the inspiration and expiration portions.

23. The system of claim 15, wherein the jacket surrounds one or more additional respiratory circuit components.

* * * * *

UNITED STATES PATENT AND TRADEMARK OFFICE
CERTIFICATE OF CORRECTION

PATENT NO.    : 6,470,888 B1
DATED         : October 29, 2002
INVENTOR(S)   : Matter It is certified that error appears in the above-identified patent and that said Letters Patent is hereby corrected as shown below:

Column 12,
Line 15, change "connection" to -- connecting --.

Signed and Sealed this

Sixth Day of May, 2003

JAMES E. ROGAN
*Director of the United States Patent and Trademark Office*